United States Patent [19]
Dawson

[11] Patent Number: 5,678,996
[45] Date of Patent: Oct. 21, 1997

[54] PRECISION ATTACHMENT DEVICE FOR A REMOVABLE DENTAL PROSTHESIS

[76] Inventor: Peter E. Dawson, 111 Second Ave., NE., Suite 1109, St. Petersburg, Fla. 33701

[21] Appl. No.: 393,722

[22] Filed: Feb. 24, 1995

[51] Int. Cl.$^6$ .............. A61C 13/12; A61C 13/225
[52] U.S. Cl. ........................ 433/177; 433/181
[58] Field of Search .................... 433/172, 177, 433/181, 182, 183

[56] References Cited

U.S. PATENT DOCUMENTS

| | | | |
|---|---|---|---|
| 2,668,353 | 2/1954 | Quellman | 433/177 |
| 2,688,799 | 9/1954 | Fluckiger et al. | 433/177 |
| 2,748,480 | 6/1956 | Weissman | 32/5 |
| 3,057,067 | 10/1962 | Morandi | 32/5 |
| 3,089,242 | 5/1963 | Weissman | 32/5 |
| 3,094,778 | 6/1963 | Mailland | 433/177 |
| 3,216,111 | 11/1965 | Sink | 433/177 |
| 3,304,610 | 2/1967 | Weissman | 32/5 |
| 3,380,161 | 4/1968 | Weissman | 32/5 |
| 3,990,150 | 11/1976 | Giovannini | 32/5 |
| 4,345,901 | 8/1982 | Romagnoli | 433/172 |
| 4,348,181 | 9/1982 | Dawson | 433/172 |
| 4,406,622 | 9/1983 | Yoon | 433/172 |
| 4,474,499 | 10/1984 | Pedrazzini | 433/181 |
| 4,547,156 | 10/1985 | Hader | 433/172 |
| 4,609,355 | 9/1986 | Harvey et al. | 433/181 |
| 4,661,069 | 4/1987 | Weissman | 433/183 |
| 4,850,869 | 7/1989 | Steinfort et al. | 433/172 |
| 4,957,438 | 9/1990 | Bax | 433/180 |
| 4,973,249 | 11/1990 | Silvio et al. | 433/182 |
| 5,098,295 | 3/1992 | Durr et al. | 433/172 |
| 5,106,299 | 4/1992 | Ghalili | 433/172 |
| 5,211,561 | 5/1993 | Graub | 433/169 |
| 5,275,560 | 1/1994 | Obersat | 433/177 |

FOREIGN PATENT DOCUMENTS 1202335 1/1960 France .................. 433/177

Primary Examiner—Nicholas D. Lucchesi

[57] ABSTRACT

The present invention is a precision attachment device for securing a removable dental prosthesis in the mouth, comprising a first section operatively arranged to be secured to a fixed tooth, a second section operatively arranged to be secured within the prosthesis, and also arranged to matingly engage the first section, the second section having a first mating member having a throughbore therein, and also having an elongated casing rotatably disposed within the throughbore of the first mating member; a spring loaded plunger member disposed within the casing and projecting therefrom, and, a retention member within the rotatable casing for limiting the extent of longitudinal travel of the plunger member.

7 Claims, 9 Drawing Sheets

PRECISION ATTACHMENT DEVICE FOR A REMOVABLE DENTAL PROSTHESIS

FIELD OF THE INVENTION

The present invention relates generally to a removable dental prosthesis. More particularly, the present invention relates to a novel precision attachment device for securing a removable dental prosthesis in the mouth.

BACKGROUND OF THE INVENTION

During the course of various dental procedures, a dental prosthesis may be installed in the mouth which is secured onto adjacent fixed dentition. Such dental prosthesis is arranged so that it can be secured to the fixed dentition, where it is removable under various conditions. For example, partial dentures and removable bridge work are securably inserted in place in the mouth. However, for cleaning and maintenance, they must be removable.

Numerous devices have been provided for this purpose, all of which provide both the fixed and removable features. There is generally a choice between intracoronal attachments, where the female component is anchored to the natural tooth or implant, and extracoronal attachments, where the male component is anchored to the natural tooth or implant. The critical aspect of such devices is to retain the dental prosthesis secured in position during actual use so as to avoid all types of rotation, lateral movement, and displacement of the removable prosthesis from its proper position in the mouth. Any such movement or displacement can cause a disturbance and annoyance to the patient during use.

Numerous holding devices of the above type have been known in the art. For example, U.S. Pat. No. 3,089,242 discloses a device where a ring is attached to the dental prosthesis and is slid downward into a channel which is secured into the side of a fixed tooth. U.S. Pat. No. 3,380,161 discloses a detent mechanism inserted in an artificial tooth which engages a recess formed in an adjacent natural tooth. Another such detent mechanism is described in U.S. Pat. Nos. 3,304,610 and 2,748,480. U.S. Pat. No. 4,973,249, discloses an extracoronal activatable precision attachment having a male component which is secured to the natural tooth or implant, and a female component which is securable thereto and is to be connected to the tooth substitute. U.S. Pat. No. 5,211,561 discloses a coupling device for removable dental prosthesis. U.S. Pat. No. 5,106,299 discloses a dental prosthesis for use with an oral implant and method of installation. U.S. Pat. No. 5,098,295 discloses a plug connection for the detachable fitting of a prosthesis structure. U.S. Pat. No. 4,850,869 discloses a removable dental prosthesis which has a primary member coupled to a secondary member by the use of a bar member. U.S. Pat. No. 3,057,067 discloses a hinge joint for releasably securing artificial dentures or prosthesis in place. U.S. Pat. No. 4,474,499 discloses a method for constructing an attachment connection between a dental prosthesis and an anchoring tooth or crown. U.S. Pat. No. 5,275,560 discloses a friction element for anchoring one removable telescopable part of a dental prosthesis on another. U.S. Pat. No. 4,957,438 discloses a dental coupling assembly for anchoring a prosthesis in the mouth. U.S. Pat. No. 4,406,622 discloses a removable attachment for partial denture comprising a connector body and a slider member. U.S. Pat. No. 4,547,156 discloses a female part of a coupling for fixing a dental prothesis in the mouth. U.S. Pat. No. 3,990, 150 discloses a dental prosthesis attachment having a fixed portion and a detachable portion, the fixed portion comprising a slide. U.S. Pat. No. 4,609,355 discloses a permanent dental prosthesis and a method of installing the prosthesis in the mouth of a patient to replace a missing tooth.

U.S. Pat. No. 4,345,901 discloses a connecting apparatus for removable dental prosthesis comprising a frustoconical male element attached to a base, a female part composed of a block having a frustoconical cavity matching the male element so that the female part can be fitted over the male element, a tubular sleeve accommodates a sliding member which is biased axially by a spring held in place by a cap screwed on one end of the sleeve, and a tip attached to a threaded section at the end of the sliding member remote from the spring makes it possible to displace the sliding member axially against the bias of the spring. When the block is fitted over the male element, a section of the sliding member is caught by the edge of the oblique groove and moved axially, then enters the transverse groove, thereby interlocking the male element and the female part.

U.S. Pat. No. 4,348,181, discloses a retaining device for removably securing a dental prosthesis in position. The retaining device includes a male section for securement to the side of the fixed tooth and a cooperating female section for securement within the dental prosthesis. The male section includes a projection which is received in an inverted U-shaped housing at the forward end of the female section. A spring loaded plunger member positioned within the female section projects form the housing and engages in a recess provided in the male projection thereby locking the two sections together. With the male member permanently fixed in the fixed tooth, the dental prosthesis having the female section secured therein can be downwardly inserted so that the U-shaped housing fits over the male projection and engages onto it. The plunger locks into the recess in the male projection to secure the dental prothesis in place.

U.S. Pat. No. 4,661,069 discloses a retaining device for removably securing a dental prosthesis in position. The retaining device includes a male section which can be secured to the side of a fixed moth and a cooperating female section which can be secured within the dental prosthesis. The male section includes a projection which is received in an inverted U-shaped housing at the forward end of the female section. A channel member upwardly extending from the housing provides a keyway for receiving a key upwardly extending from the projection, to maintain a secure stability between the male and female sections. A spring loaded plunger member positioned within the female section extends into the housing and engages a recess formed in the projection, thereby locking the two sections together.

While the above mentioned retaining devices have been found most useful, further improvements in such retaining devices is necessary in order to obtain an interchangeable precision attachment having better flexibility of positioning. Further, improving stability between the male and female sections to avoid any possible movement or displacement therebetween is also desirable.

SUMMARY OF THE INVENTION

The present invention is a precision attachment device for securing a removable dental prosthesis in the mouth, comprising a first section operatively arranged to be secured to a fixed tooth, a second section operatively arranged to be secured within the prosthesis, and also arranged to matingly engage the first section, the second section having a first mating member having a throughbore therein, and also having an elongated casing rotatably disposed within the throughbore of the first mating member; a spring loaded plunger member disposed within the casing and projecting therefrom, and, retention means within the rotatable casing for limiting the extent of longitudinal travel of the plunger member.

Accordingly, the primary object of the present invention is to provide an improved precision attachment device for securing a removable dental prosthesis in the mouth.

Another object of the present invention is to provide such a device having securing means which permits flexibility of positioning within the mouth.

A further object of the present invention is to provide such a device which is compatible with a wide array of removable partial denture designs.

A further object of the present invention is to provide such a device which facilitates securement of the device in order to ensure stability.

A further object of the present invention is to provide such a device which permits easy insertion of the device in the removable and fixed parts of the teeth and assures suitable alignment and parallelism of the parts.

A further object of the present invention is to provide such a device which can be easily placed using a positioning matrix system.

A further object of the present invention is to provide such a device which permits easy replacement of the parts of the device.

DESCRIPTION OF THE PREFERRED EMBODIMENT

Figure 1:
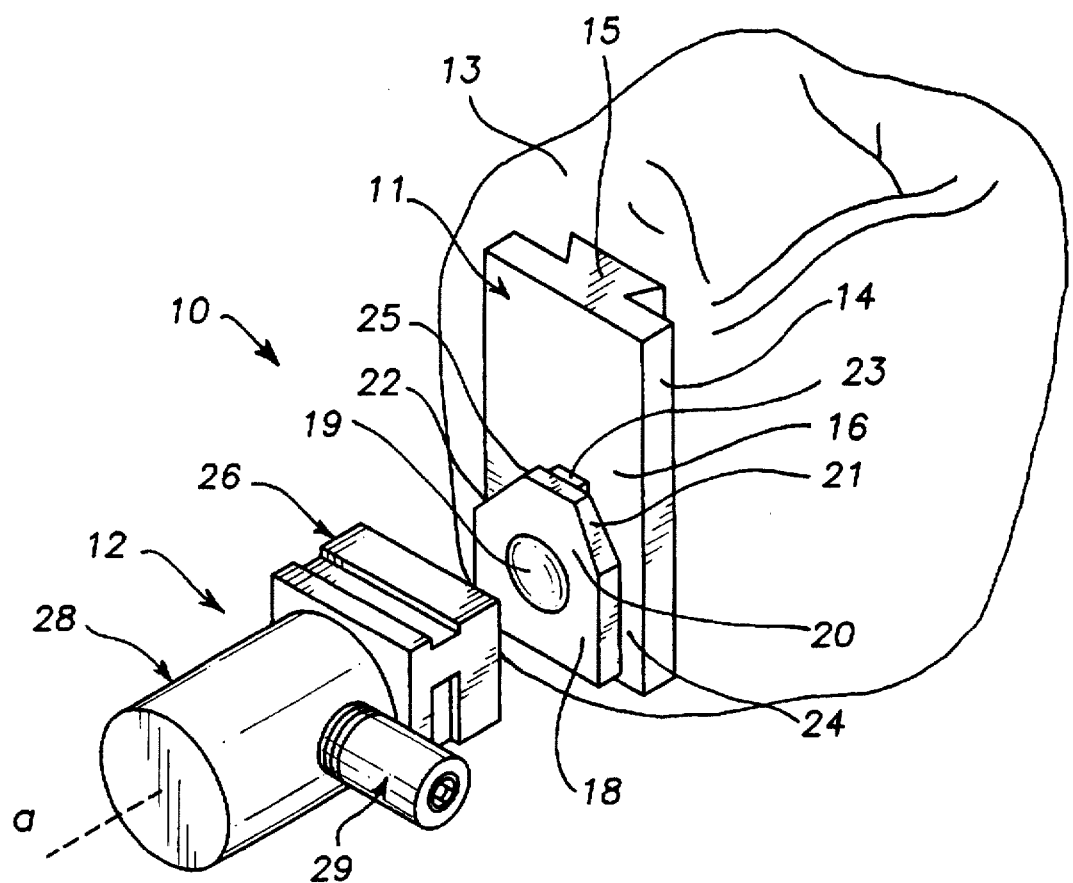
FIG. 1 illustrates an extracoronal embodiment of the precision attachment device.

At the outset, it should be clearly understood that the drawings are to be read together with the specification, and are to be considered a portion of the entire "written description" of this invention, as required by 35 U.S.C. §112. Also, identical reference numerals on different figures refer to identical elements of the invention.

Figure 2:
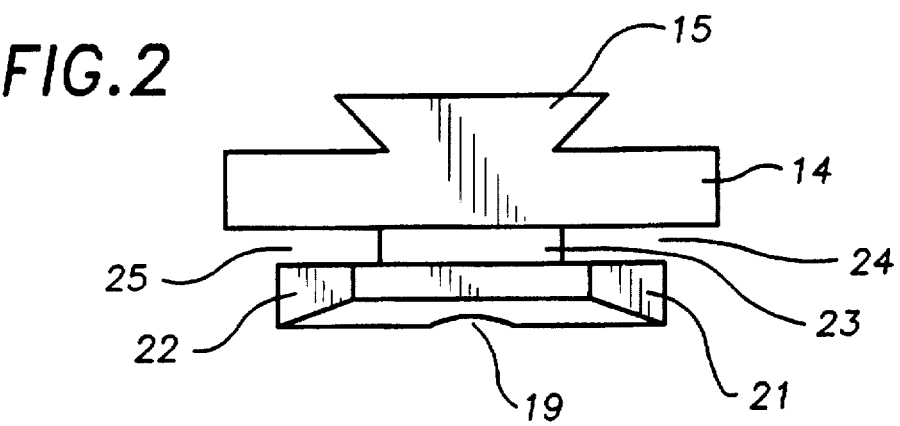
FIG. 2 is a top view of the first section 11 of the device illustrated in FIG. 1.

FIG. 1 illustrates an extracoronal embodiment of the device, shown generally at 10. In this embodiment, first section 11 is secured to the side of fixed tooth 13 (the first section may alternatively be secured to an implant), and cooperating second section 12 would be secured within the dental prosthesis (not shown). The first section 11 includes a solid rectangular plate 14 from which extends toward the rear a dovetail spline 15. The height of the spline 15 extends the entire height of the plate 14. Protruding from the front face 16 of the plate 14, and extending only from the lower half thereof, is a first member 23. Protruding from first member 23 is projecting block 18, which constitutes a recessed member, the block 18 having a narrower width than the plate 14, and a wider width than first member 23. Formed into the projecting block 18 is a recess 19, and above the recess 19 is provided a cam surface 20 formed as a cut out at the upper edge of the block 18. The upper edge and sides of the block 18 are tapered or beveled to provide beveled surfaces 21 and 22. On either side of the block 18 there is provided undercut channels 24 and 25, better shown in FIG. 2, for receiving a portion of the female section 12, as will hereinafter be explained.

Second section 12 comprises a first mating member 26 which is operatively arranged to mate with block 18, and rotatable casing 28, which is rotatable about axis α. In this first embodiment, section 12 would be encased within the dental prosthesis (not shown). Before the prosthesis is made, casing 28 is free to rotate, but, once encased in the prosthesis, is fixedly secured, and not rotatable. Also shown in FIG. 1 is retention assembly member 29, which is threaded into casing 28, which retention member will be discussed in detail infra.

Figure 3A:
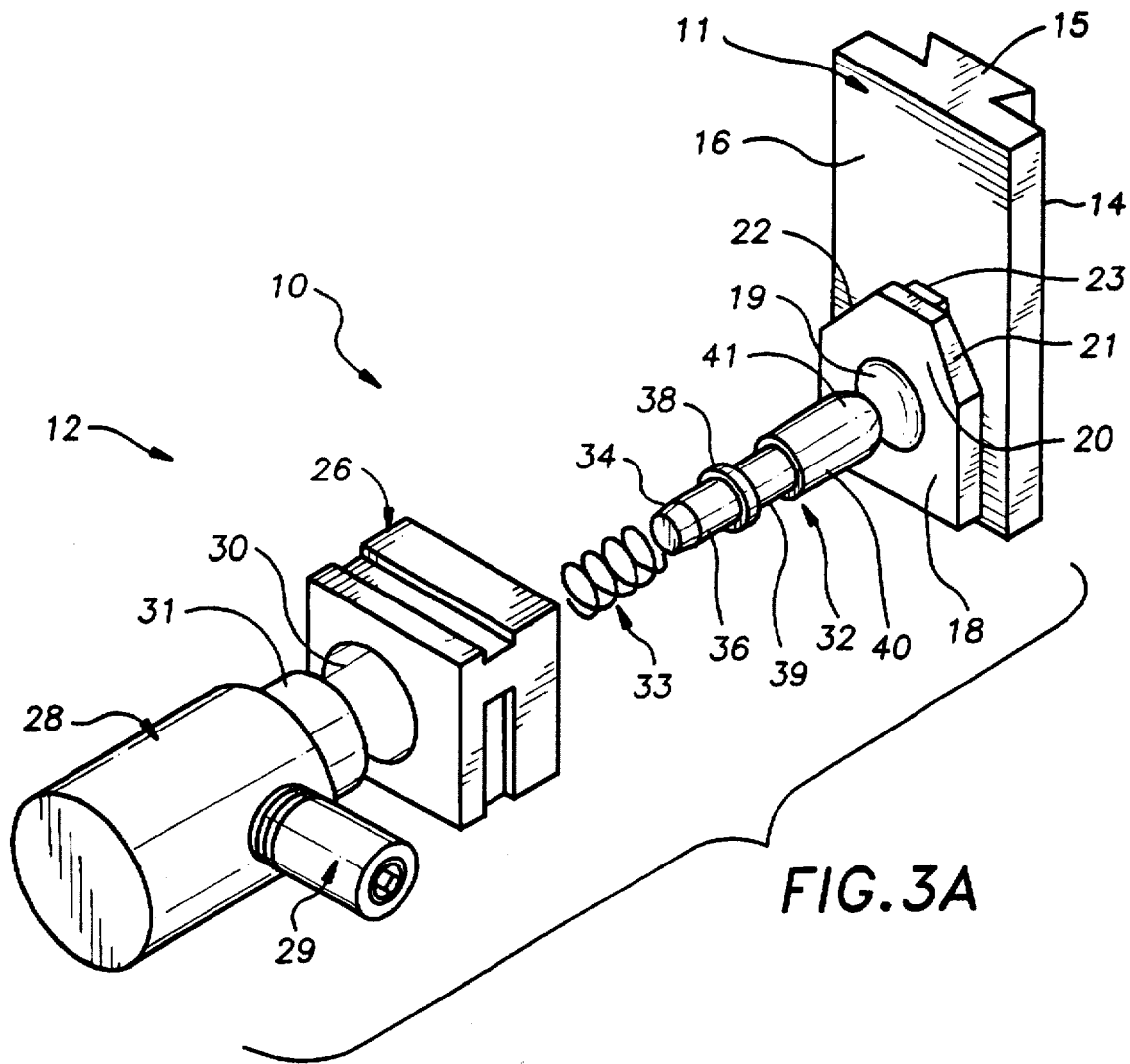
FIG. 3 A is an exploded view of the unassembled extracoronal embodiment of the invention illustrated in FIG. 1.
FIG. 3B is an exploded view similar to FIG. 3A, shown from a different angle.
FIG. 3C is an elevational sectional view taken through the extracoronal embodiment of the precision attachment device when the first section and second sections thereof are in an assembled, engaged position.
FIG. 3D is a perspective view of the extracoronal embodiment of the precision attachment device when the first section and second sections thereof are in an assembled, engaged position.

FIG. 3A is an exploded view of the extracoronal embodiment of the invention illustrated in FIG. 1. First mating member 26 is shown to include throughbore 30. Cylindrical casing 28 is shown to include cylindrical extension member 31, which has a smaller diameter than the casing itself. The outer diameter of extension member 31 is slightly smaller than the diameter of throughbore 30, such that, when extension member 31 is inserted into the throughbore, casing 28 is free to rotate therein.

Also as shown in FIG. 3A, a coil spring 33, having closed end loops at both ends thereof, is mounted within a partial throughbore in casing 28, and functions to bias plunger member 32. The body portion 36 of the plunger member together with the tapered rear section 34, extends into the center of coil spring 33. The spring acts upon circular collar section 38 of the plunger member. The plunger also includes neck portion 39 which extends between collar 38 and collar section 40. At the distal end of collar section 40 is spherical projection 41, which is designed to matingly engage concave recess 19 of block 18.

Figure 4:
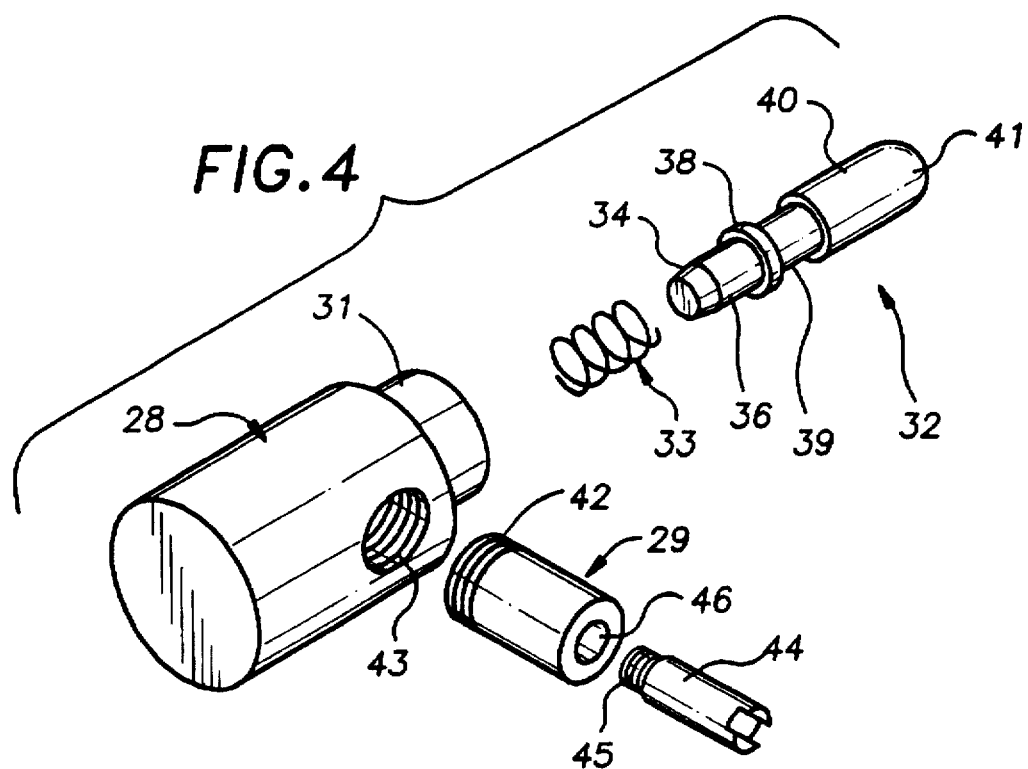
FIG. 4 is an exploded perspective view of the plunger member and plunger retention assembly of the invention.

The movement of plunger member 32 is limited by retention assembly member 29, shown in more detail in FIG. 4. Assembly member 29 comprises a hollow cylindrical shell having threads 42 at one end. Threads 42 engage threaded bore 43 in casing 28 to hold the retention assembly in place. Set screw 44 is insertable in bore 46 of retention member 29, and threaded section 45 engages a threaded bore (not shown) internal to casing 28. When plunger member 32 is pushed into position within casing 28, set screw 44 is threaded into the casing, such that threaded section 45 aligns with neck 39. As the set screw is tightened, its threaded end restricts movement of the plunger by interfering with collar sections 38 and 40, respectively. Thus, the plunger member is captured within casing 28 but is free to axially move within bore 30 a distance corresponding to the length of neck section 39.

Figure 3B:
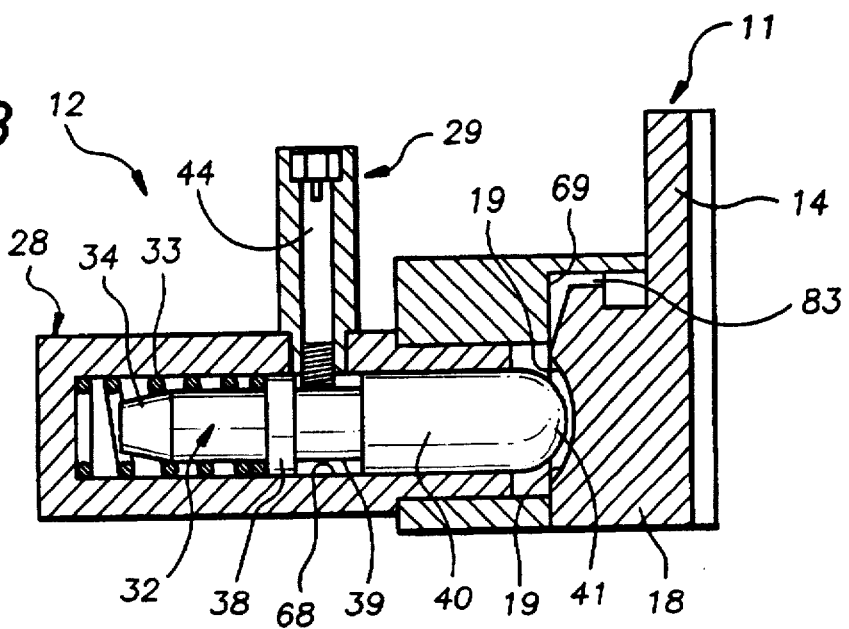
Figure 3C:
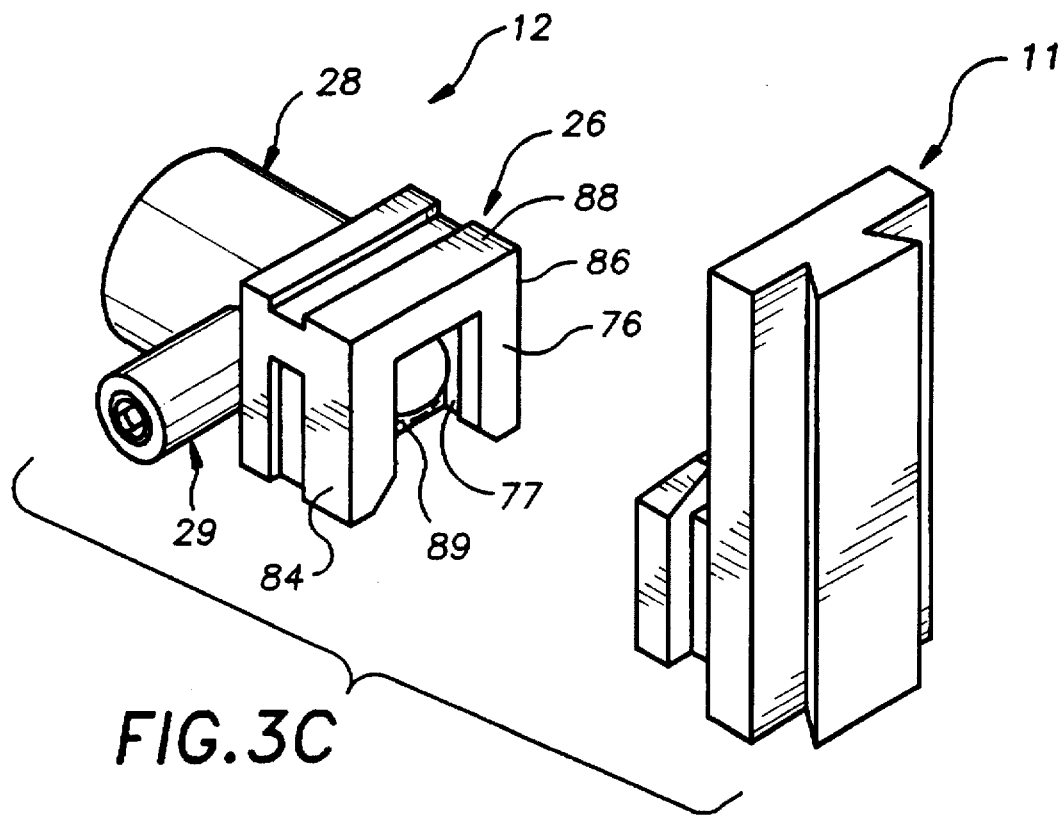
Figure 3D:
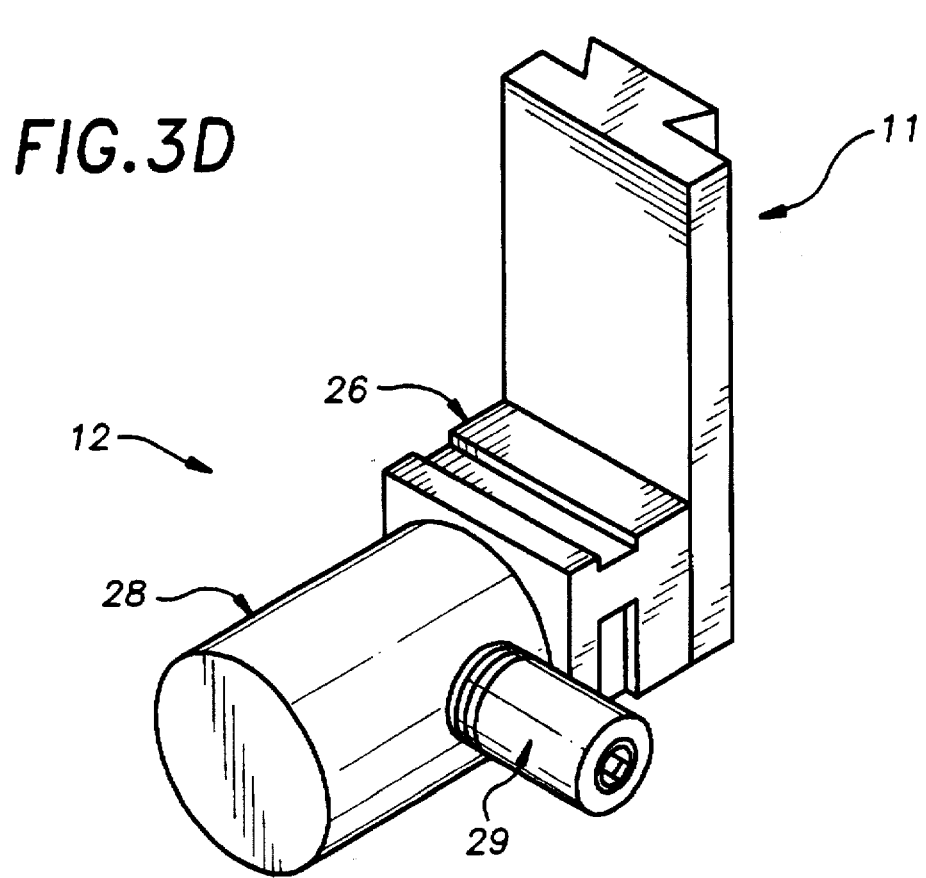

FIG. 3C illustrates the device shown in FIG. 3A from a different angle, and also shows the plunger locked into place within mating member 26. Second section 12 is shown to comprise mating member 26, casing 28 and retention mechanism 29. At the front of section 12, mating member 26 is seen to have an inverted U-shaped portion including side section 84 and 86 and top section 88. The front facing 89 within the hollow of the front portion is spaced from the outer front face 76 of mating member 26, with the side walls of the hollow being undercut at 77 adjacent to the front facing 76.

As shown in FIG. 3B, a longitudinal bore 68 extends from the front facing 69 of second section 12 inwardly through the various sections of casing 28. Positioned within bore 68 is plunger member 32. FIG. 3B shows clearly how set screw 44 aligns with neck 39 of plunger 32 and restricts its axial movement within the casing.

When assembled as shown in FIG. 3B, projecting block 18, extending forward of plate 14, is received within the inverted U-shaped portion at the front of the casing 28, with the undercuts 24, 25 of block 18 and the undercuts 77 (shown in FIG. 3C) within the hollow of mating member 26 providing a tongue and groove engagement to prevent relative rotation therebetween. The plunger member 32 extends into the recess 19 formed in projecting block 18 to secure sections 11 and 12 together.

The parts are arranged so that the first section 11 can initially be secured to the side of a fixed tooth or implant, and the second section 12 will then be inserted into the dental prosthesis. The two sections 11 and 12 are first located so that they are adjacent to each other, and then the dental prosthesis carrying the section 12 is vertically moved downward into position. The housing at the front of casing 28 will then move onto the projecting block 18, being guided by beveled surfaces 21 and 22 to position the projecting block 18 within the inverted U-shaped housing in tongue and groove engagement therebetween. At the same time, the plunger member 32 will be guided by means of the beveled surface 20 into recess 19 provided in projecting block 18.

It should be noted that the projecting block 18 on the first section 11 is situated within the inverted U-shaped housing of the second section 12, and the plunger member 32 is situated within recess 19. The spring 33, biasing the plunger member, holds the plunger member tightly within the recess 19 and locks the projecting block 18 within the housing of the second section 12. Accordingly, a secure locking arrangement is provided. However, it should also be noted that there is slight vertical movement permitted by means of the plunger member which can move vertically within the recess 19, the projecting block 18 being smaller than the height of the housing hollow and accordingly provides a clearance 83. This clearance 83 permits the prosthesis containing the second section 12 to be pressed against the gum for the approximation of a feeling of elasticity of a living bone in the human mouth, so that the prosthesis, when inserted in the mouth, more nearly feels like natural teeth to the wearer. At the same time, the holding device provides a secure engagement which prevents wobble and provides the necessary security to hold the dental prosthesis in place, wherein the plunger member 32 will seat itself in the recess 19 in the position shown in FIG. 3B when there is no applied pressure on the prosthesis.

The prosthesis can be removed by pulling upward on the prosthesis. This upward pull will force the spherical surface 41 of the forward end of the plunger to move inward of the casing 28 as it is pulled upward in the recess 19. The movement inwardly of the plunger member releases the engagement between the first section 11 and the second section 12, and allows the dental prosthesis to be removed.

Figure 5:
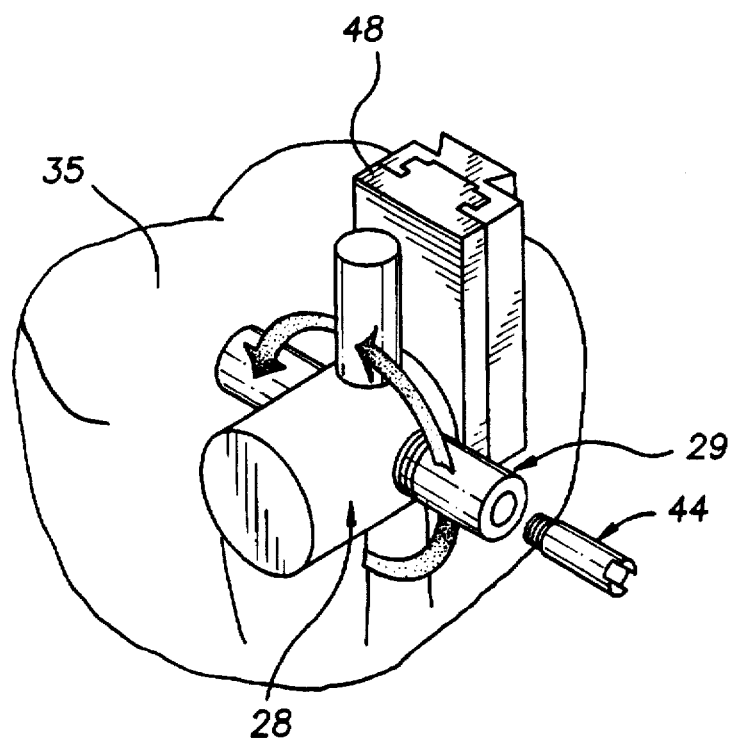
FIG. 5 illustrates one embodiment of the second section of the device implanted in a dental prosthesis, also illustrating the ability of the casing and plunger retention mechanism to rotate 360° prior to encasement in the prosthesis.
Figure 6:
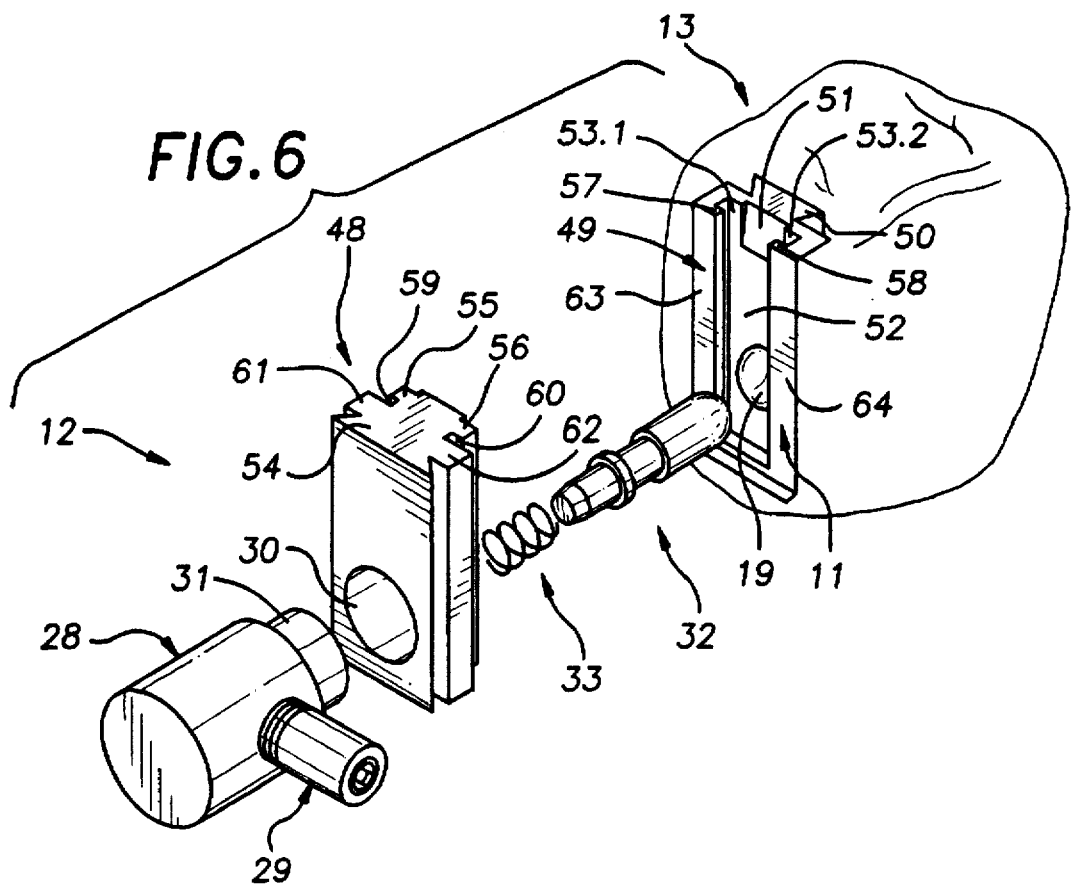
FIG. 6 illustrates in exploded perspective an intracoronal embodiment of the precision attachment device.

FIG. 6 illustrates an intracoronal embodiment of the invention. In this embodiment, first section 11 comprises an open rectangular slotted member 49 which is mounted to tooth 13. Member 49 comprises a dovetail 50 which mounts in a corresponding dovetail groove in tooth 13. Member 49 contains a backplate 52 having a recess 19 therein to receive plunger member 32. The backplate also contains beveled surface 51 which functions to guide the plunger into position as the prosthesis is being installed. Member 49 also contains channels 52 and 53 which receive a portion of second section 12 to lock the prosthesis in place. Second section 12 comprises mating section 48 and casing 28 with its attached retention mechanism 29. Section 48 has a throughbore 30 therein to receive cylindrical extension 31 of casing 28. As in the extracoronal embodiment, the casing is rotatable within the bore of the mating section. Section 48 comprises dovetail section 54 which functions to secure section 12 in a dovetail groove of the prosthesis. Section 48 also comprises rectangular extensions 55 and 56 which engage channels 52 and 53, respectively, of member 49. Similarly, extensions 57 and 58 of member 49 engage channels 59 and 60 of member 48 when the two sections 11 and 12 are matingly engaged. Finally, front surfaces of extensions 61 and 62 of member 48 mount flush with facing surfaces 63 and 64, respectively, of member 49, ensuring a stable and sanitary fit. Operation of the intracoronal embodiment is identical to operation of the extracoronal embodiment described earlier. It is important to note, however, that the plunger member and casing/retention assembly is identical in both embodiments. Also, as shown in FIG. 5, prior to manufacture of the prosthesis 35 which encases second section 12 in this embodiment, casing 28 is free to rotate 360°.

Figure 7:
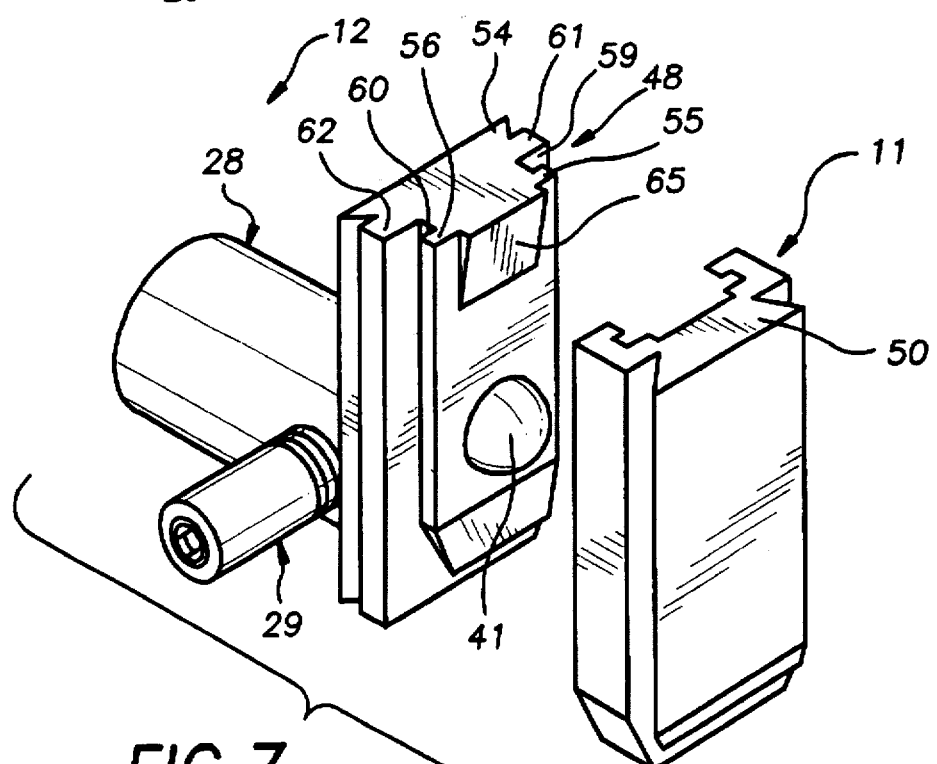
FIG. 7 is a perspective view of the intracoronal embodiment shown from a different angle than in FIG. 6.
Figure 8:
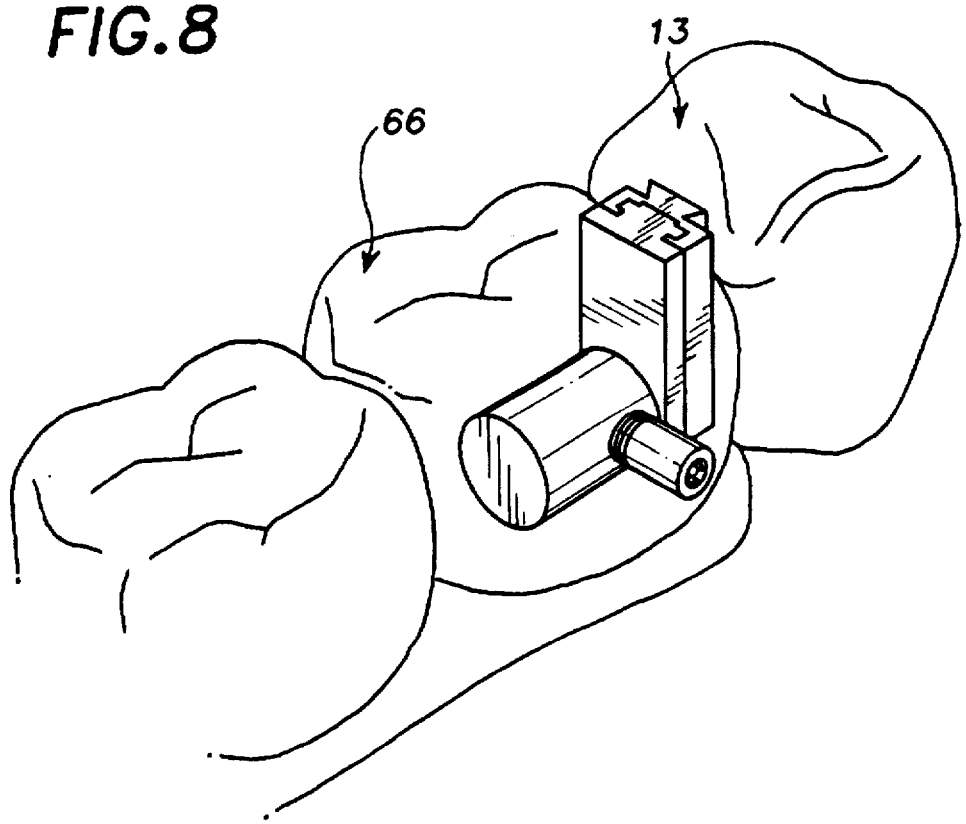
FIG. 8 illustrates the second section of the intracoronal embodiment embedded in prosthesis and locked to the first section which is secured to tooth 13.

FIG. 7 is a perspective view of the intracoronal embodiment shown from a different angle than in FIG. 6, showing the plunger locked in place, such that only spherical surface 41 is exposed. This view also shows extension 65 which mates with beveled surface 51 when section 12 is inserted downwardly into section 11. FIG. 8 illustrates the second section of the intracoronal embodiment embedded in prosthesis 66 and locked to the first section which is secured to tooth 13.

Figure 9:
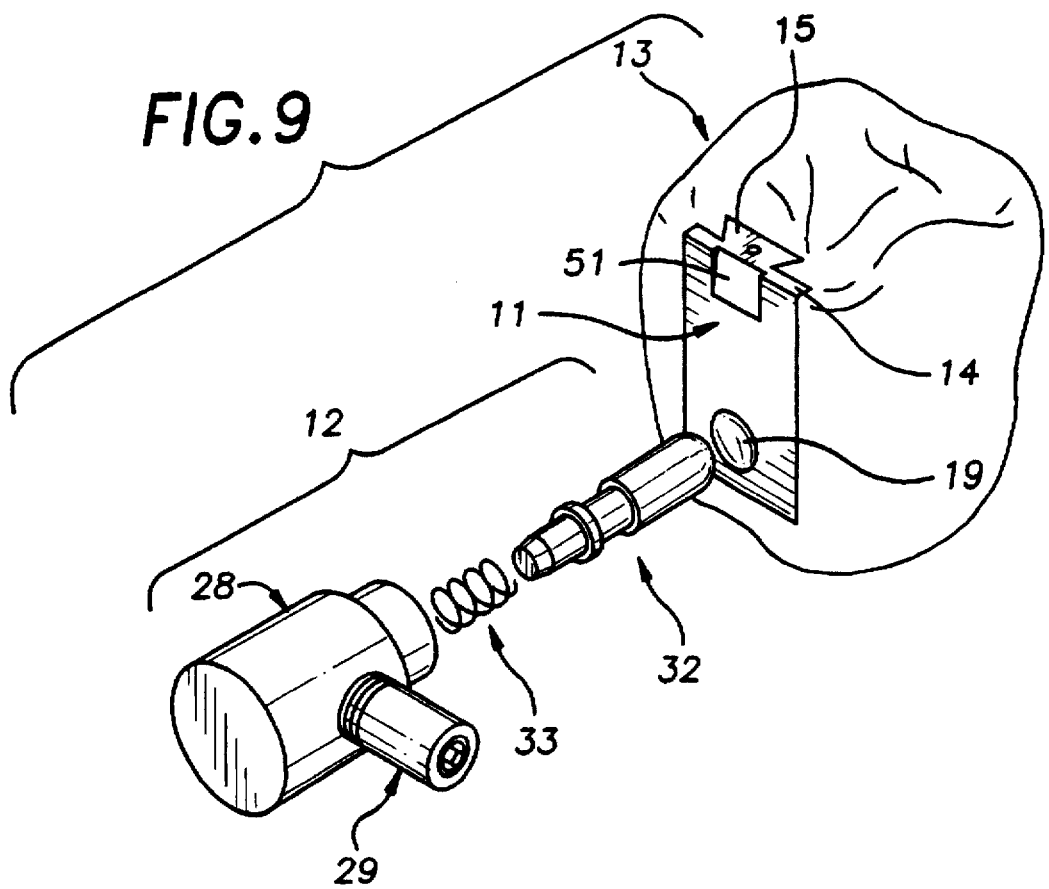
FIG. 9 illustrates an alternative embodiment of the invention.

FIG. 9 illustrates yet another embodiment of the invention. In this embodiment, first section 11 comprises rectangular plate 14 having dovetail 15 protruding from the back thereof, which dovetail engages a corresponding dovetail groove in tooth 13. The plate also has a beveled surface 51 on its face to guide plunger 32 into engagement with concave recess 19. Second section 12 comprises casing 28, retention mechanism 29, spring 33 and plunger 32. Note that this embodiment does not include a mating member as part of section 12 as do the preceding embodiments.

Figure 10:
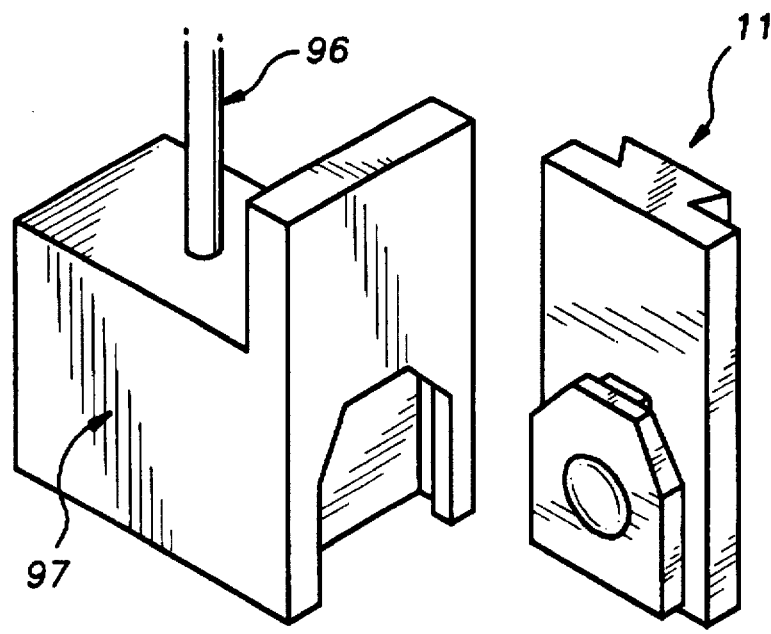
FIG. 10 illustrates a jig used to position the extracoronal embodiment of the invention.
Figure 11:
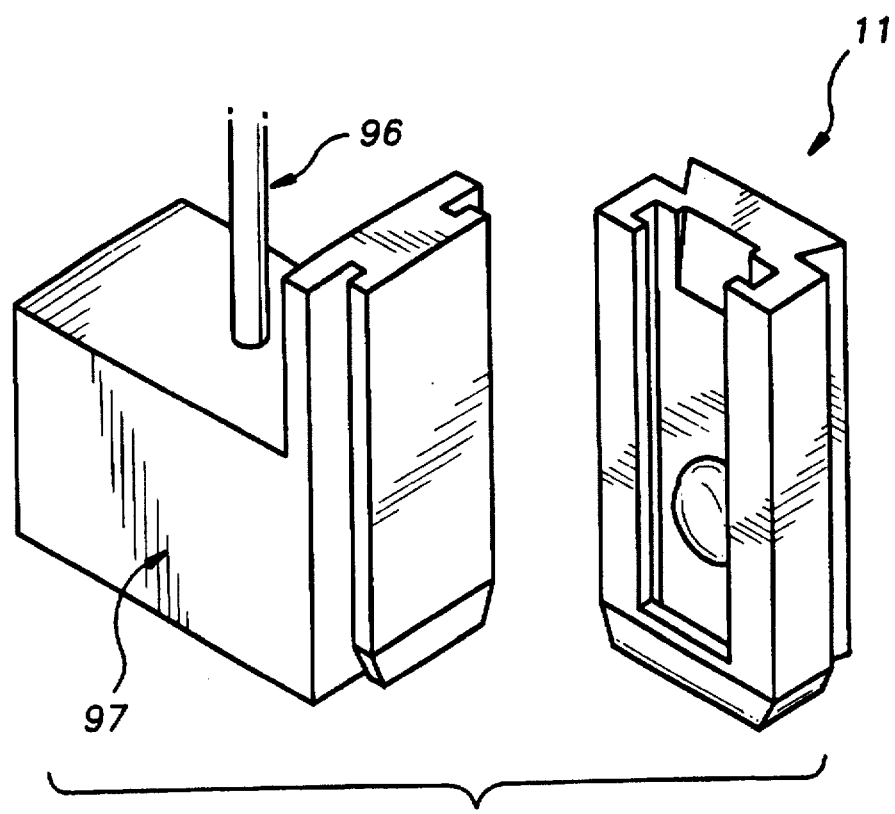
FIG. 11 illustrates a jig used to position the intracoronal embodiment of the invention.
Figure 12:
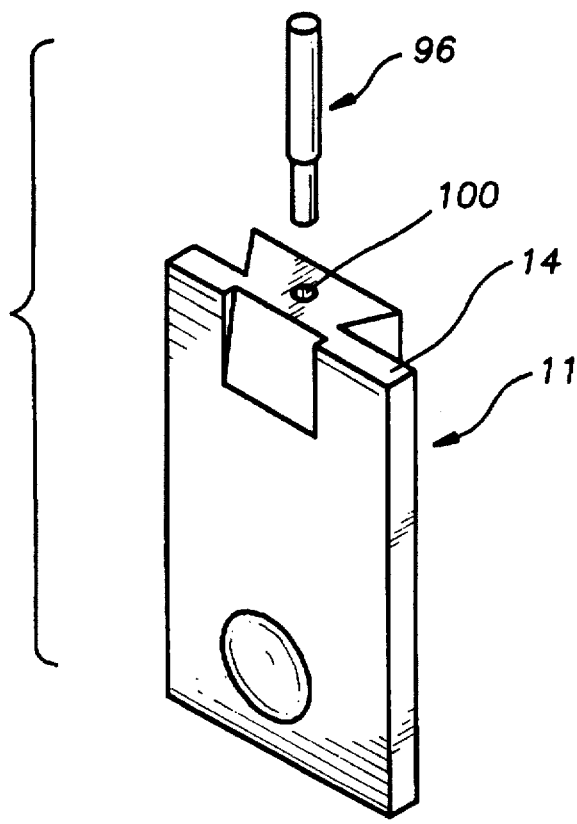
FIG. 12 illustrates how a universal mandrel can be used to position section 11 of the embodiment shown in FIG. 9.

In order to accurately position the first section 11 within the fixed tooth, a universal mandrel is used. A mandrel is a device which, when placed in a positioning device (e.g., paralleling matrix, etc.), is used in relation to either the matrix or patrix to ensure that the removable prosthesis can be inserted or removed without difficulty. (A patrix is a male dental pattern. A matrix is a pattern that has a concavity in which a patrix is matingly received.) As shown in FIG. 10, universal mandrel 96 and positioning matrix 97 is used to position section 11 of the extracoronal embodiment shown in FIG. 1. As shown in FIG. 11, universal mandrel 96 is used in conjunction with positioning matrix 99 to position section 11 of the intracoronal embodiment shown in FIG. 6. FIG. 12 illustrates how universal mandrel 96 can also be used to position section 11 of the embodiment shown in FIG. 9 by engaging bore 100 of plate 14.

Figure 13:
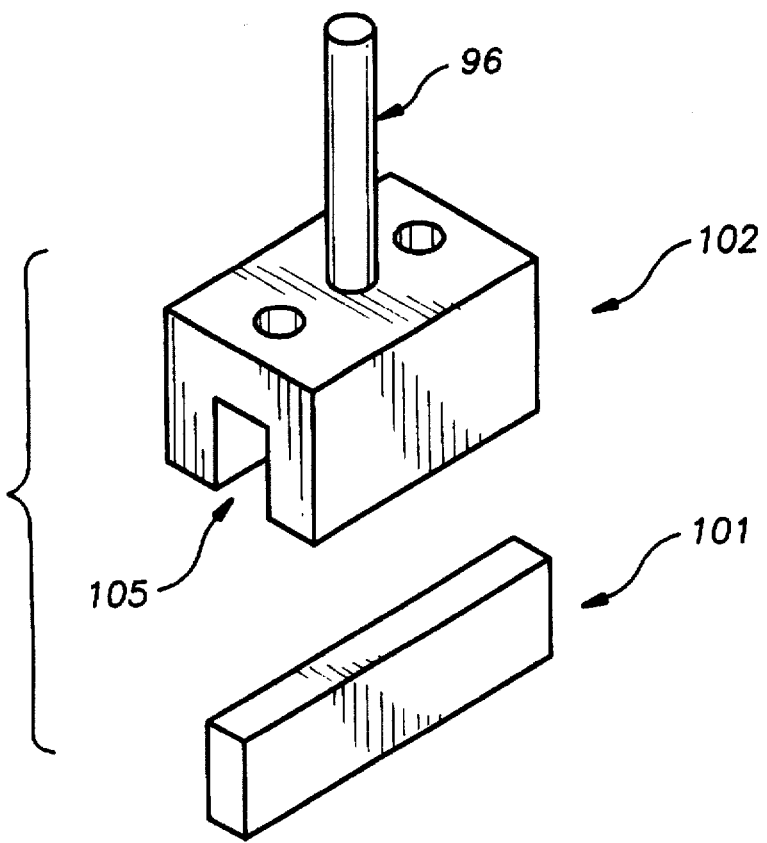
FIGS. 13 illustrates another embodiment of the present invention;.

FIG. 13 illustrates yet another embodiment of the invention. In this embodiment, rectangular bar is positioned between two abutments (crowns, caps, etc.), by rectangular positioning matrix 102, which is comprised of positioning matrix 105 and universal positioning mandrel 96. This embodiment allows stabilization of the removable prosthesis and the splinting together of the abutments or teeth being restored.

Figure 14:
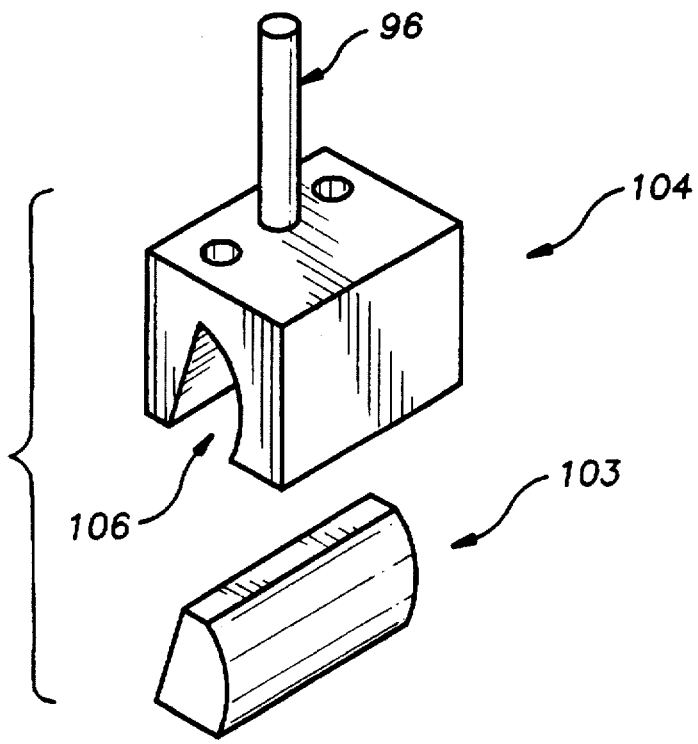
FIG. 14 illustrates still another embodiment of the invention.

FIG. 14 illustrates yet another embodiment of the invention. In this embodiment, retention bar 103 is positioned in a manner that allows for a path of insertion as shown in FIG. 15, yet stabilizes the removable appliance from dislodgement during the mastication of food. FIG. 103 is positioned by the positioning matrix 104 in conjunction with universal mandrel 96.

Figure 15A:
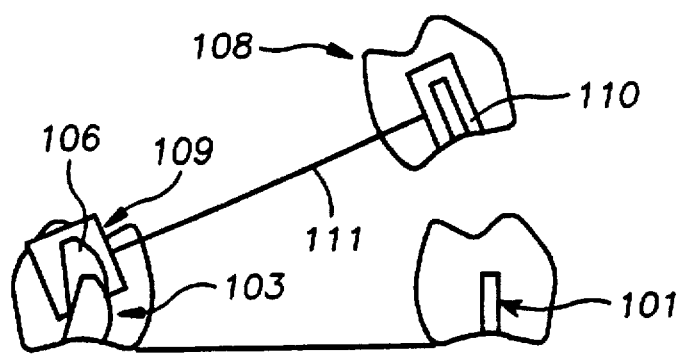
FIG. 15A to 15C illustrate operation of the embodiments depicted in FIGS. 13 and 14.
Figure 15B:
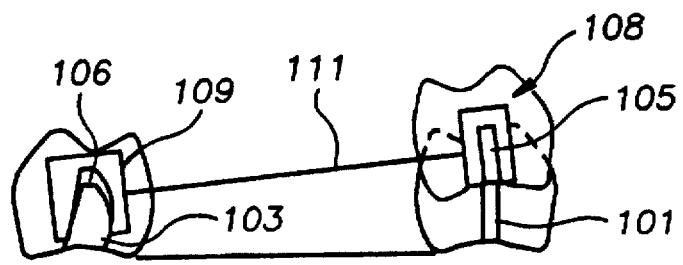
Figure 15C:
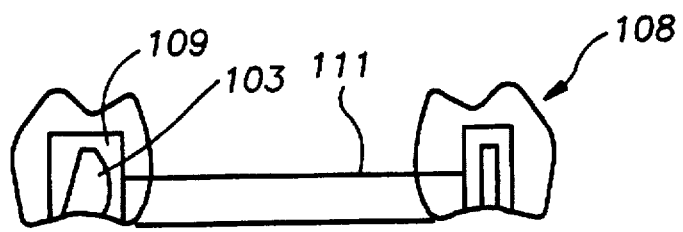

FIG. 15A-15C, which are cross-sections through a dental arch, illustrate how bars 101 and 103 work in conjunction with each other during installation of a removable prosthesis, indicates parallelism, path of insertion, and the rotation of the removable appliance. In practice, the retention bar 103 is inserted first, and then the rectangular bar 101 is rotated into position to stabilize the removable appliance. In these views, 106 represents a bar attachment, 108 the removable prosthesis, 109 a female positioning component, 110 an extracoronal attachment of this invention, and 111 a structure which extends between the female positioning component 109 and the extracoronal attachment to insure proper insertion.

Thus, it is seen that the present invention comprises several embodiments of a precision attachment device for a removable dental prosthesis. All embodiments are designed to accept an interchangeable plunger member and plunger retention member. The retention member is rotatable to facilitate accessibility within the mouth. The plunger may be easily removed for cleaning or maintenance.

It will be understood that the foregoing description is illustrative of the invention and should not be considered as limiting and that other embodiments of the invention are possible without departing from the invention's spirit and scope, as embodied in the following claims.

What is claimed is:

1. A precision attachment device for securing a removable dental prosthesis in the mouth to a fixed tooth, comprising:

a first section (11) operatively arranged to be secured to the fixed tooth (13);

a second section (12) operatively arranged to be secured within the removable dental prosthesis (35 or 66), and also arranged to non-rotatably matingly engage the first section (11), the second section (12) having a first mating member (26) having a throughbore (30) therein, the first mating member (26) being adapted to be non-rotatably coupled to the first section (11), an elongated rotatable casing (28) rotatably disposed within the throughbore (30) of the first mating member (26), the casing having a laterally projecting portion, a plunger member (32) disposed within the rotatable casing (28) and projecting therefrom and operable to hold the first mating member (26) to the first section (11), spring means (33) mounted within the rotatable casing (28) and operable to bias the plunger member outwardly of the casing, and retention means (29) carried by the laterally projecting portion of the rotatable casing (28) for rotational movement therewith, the retention means (29) limiting the extent of axial travel of the plunger member (32).

2. The precision attachment device as recited in claim 1 wherein the first section (11) includes a plate (14) having a first member (23) projecting from one side of said plate (14) and a dovetailed spline (15) projecting from an opposite side of said plate (14), wherein the dovetailed spline (15) is adapted to matingly engage a corresponding dovetailed groove in the fixed tooth (13), and the first member (23) is adapted to be non-rotatably coupled to the rotatable casing (28).

3. The precision attachment device as recited in claim 2 wherein said first section contains a projecting block extending from said first member to form a pair of channels between said plate and said projecting block to receive a portion of said second section.

4. The precision attachment device as recited in claim 3 wherein the projecting block (18) of the first section (11) contains a recess (19) to receive the plunger member (32) and also contains a cam surface (20) vertically positioned above the recess (19) to guide the plunger member (32) into the recess.

5. The precision attachment device as recited in claim 1 wherein the elongated rotatable casing comprises a cylindrical shell having a threaded throughbore (43) therein, and wherein the retention means (29) within the rotatable casing (28) for limiting the extent of axial travel of the plunger member (32) comprises a second cylindrical shell operatively arranged to be screwed into the threaded throughbore (43), and a threaded set screw member (44) operatively arranged to be screwed into the second cylindrical shell.

6. The precision attachment device as recited in claim 1 wherein the rotatable casing (28) and attached retention means (29) are operatively arranged to rotate up to 360° about an axis (a) of the casing.

7. A precision attachment device for securing a removable dental prosthesis in the mouth, comprising:

a first section (11) operatively arranged to be secured to a fixed tooth (13), the first section including an essentially rectangular plate (14) having
- a dovetailed spline (15) protruding from one side thereof, the spline containing a bore (100) to receive a positioning mandrel (96),
- a recess (19) in a second side of the plate opposite the spline, and
- a beveled surface (51) on the second side of the plate, the beveled surface being adapted to function as a guide;

a second section (12) operatively arranged to be secured within the removable dental prosthesis (35 or 66), and also arranged to matingly engage the first section (11), the second section including

- a rotatable casing (28),
- a plunger member (32) disposed within the rotatable casing (28) and projecting therefrom,
- spring means (33) mounted within the rotatable casing (28) and operable to bias the plunger member outwardly of the casing, and
- retention means (29) within the rotatable casing (28) for limiting the extent of axial travel of the plunger member (32), wherein the spring loaded plunger member (32) functions to mate with the first section (11), the beveled surface (51) acting as a guide for insertion of the plunger member (32) into the recess (19).

* * * * *